US007838722B2

(12) United States Patent  
Blessing et al.

(10) Patent No.: US 7,838,722 B2
(45) Date of Patent: Nov. 23, 2010

(54) INDIRECT PRINTING OF AGM

(75) Inventors: Horst Blessing, Euskirchen (DE); Hans Adolf Jackels, Mechernich (DE); Siegfried Link, Schleiden (DE); Volker Maier, Euskirchen (DE); Thomas Ludwig Woschnik, Euskirchen (DE); Martin Scaife, Cologne (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/183,357

(22) Filed: Jul. 18, 2005

(65) Prior Publication Data

US 2006/0024433 A1   Feb. 2, 2006

(51) Int. Cl.
*A61F 13/15* (2006.01)
*B28B 19/00* (2006.01)
*B29C 65/00* (2006.01)

(52) U.S. Cl. .................. 604/367; 604/368; 604/374; 156/390; 156/548; 156/526

(58) Field of Classification Search ................. 604/367, 604/368, 374; 156/390, 548, 542, 526
See application file for complete search history.

(56) References Cited

U.S. PATENT DOCUMENTS

| 5,030,314 | A |   | 7/1991 | Lang et al. |
| 5,128,082 | A | * | 7/1992 | Makoui ................. 264/112 |
| 5,628,845 | A | * | 5/1997 | Murray et al. .......... 156/64 |
| 5,762,712 | A |   | 6/1998 | Soehn et al. |
| 5,830,202 | A |   | 11/1998 | Bogdanski et al. |
| 6,048,489 | A |   | 4/2000 | Reiter et al. |
| 6,730,387 | B2 | * | 5/2004 | Rezai et al. ............ 428/141 |
| 2003/0201052 | A1 |   | 10/2003 | Koslow |

FOREIGN PATENT DOCUMENTS

| EP | 0 203 289 A2 | 12/1986 |
| EP | 1088537 A2 | 4/2001 |
| JP | 11-320742 | 11/1999 |
| JP | 2003-165173 | 6/2003 |
| WO | WO 93/02861 A | 2/1993 |
| WO | WO 95/16420 A1 | 6/1995 |
| WO | WO 96/07380 A1 | 3/1996 |

OTHER PUBLICATIONS

European Search Report, mailed Sep. 9, 2005, 2 pages.

* cited by examiner

*Primary Examiner*—Jacqueline F. Stephens
(74) *Attorney, Agent, or Firm*—Laura L. Whitmer; Thibault Fayette; Eric T. Addington (57) ABSTRACT

The present invention relates to a method of applying absorbent gelling material (AGM) granules by indirect printing onto an carrier layer for use in an absorbent article, particularly diaper for babies or adults, training pants, pull-up diapers (diaper pants), sanitary napkins, panty liners or the like. These articles typically comprise the carrier layer with the AGM particles together with further layers, making up the complete article.

12 Claims, 9 Drawing Sheets

INDIRECT PRINTING OF AGM

FIELD OF THE INVENTION

The present invention relates to a method of applying absorbent gelling material (AGM) granules onto an carrier layer for use in an absorbent article, particularly diaper for babies or adults, training pants, pull-up diapers (diaper pants), sanitary napkins, panty liners or the like. These articles typically comprise the carrier layer with the AGM particles deposited thereon by indirect printing together with further layers making up the complete article.

BACKGROUND OF THE INVENTION

The term "AGM granules" as used herein includes materials capable of absorbing and storing a high amount of liquid compared with the volume thereof. "AGM" is the abbreviation of Absorbent Gelling Materials. These materials are mainly formed by superabsorbent polymers. In the present context the AGM material may be used as granules of different particle size including powder like materials or a mixture of powder material and granules of different particle size or forms (e.g. fibers).

AGM materials of this kind are usually embedded into absorbent pads of melt blown fibers or cellulose fibers (or similar fibrous materials and combinations thereof) or directly deposited onto a non-woven carrier layer. The present invention is applicable to both of these methods. This kind of "absorbent article" may be used for example for manufacturing a diaper, a sanitary towel or even a liquid gathering article of any kind.

Various approaches have been proposed for obtaining AGM granule distribution on a substrate having a predetermined pattern and thickness profile. These approaches include blowing an airborne mixture of AGM granules and fibers through a conduit onto a vacuum drum. Methods of this kind only allow a limited control of the pattern and the distribution of the thickness of the AGM over the surface onto which the AGM is distributed.

Particularly in case of low or no cellulose fiber containing absorbent cores, having AGM granules as the only liquid storage material, AGM granule distribution with accuracy with respect to shape and discreetness is highly important.

In this context it should be mentioned that it is possible to use single or multi piece cores, one layer of AGM or several layers on top of each other overlapping or besides each other. This also allows to use different AGM's in different layers. Thus the possibilities of variation of the achieved product are nearly endless. However, high accuracy of the granule distribution is important.

SUMMARY OF THE INVENTION

Thus the present invention is directed to a method for applying AGM granules onto a surface with high accuracy of the distribution, pattern and the amount of AGM material on the surface by indirect printing. Such a process method can be used in an application of AGM particles requiring accurate, print like positioning of granules or powders on a carrier layer. One particular application may be the making of primarily AGM/glue comprising cores for disposable diapers or parts of such cores.

According to a first embodiment of the present invention, the indirect printing method according to the invention is characterized in that the AGM granules are taken up by a transfer device from a bulk storage of AGM granules,
said transfer device having recesses on the surface thereof, the number, size and position of which determining the amount and pattern of AGM granules taken up by the transfer device,
the transfer device being moveable from the bulk storage to a position passed by the carrier layer (transfer or meeting position),
means being provided for retaining the AGM granules inside said recesses during movement of the transfer device to said meeting (or transfer) position,
and means being provided for expelling said AGM granules onto the carrier layer in said transfer position.

The invention further refers to an apparatus, particularly an apparatus for conducting the method according to the invention.

In the following indirect printing shall mean the transfer of AGM which is separated from the bulk storage of AGM before it is in contact with the carrier layer. Direct printing means that the AGM is not separated from the bulk storage of AGM before it is in contact with the carrier layer. This is not included in the present invention.

The present invention provides a method and apparatus which significantly increases AGM deposition accuracy. The standard deviation achieved so far has been reduced to about ¼ of what has been achieved with advanced prior technology. Thus diaper cores having an accurate distribution profile of AGM in the lateral and the longitudinal direction can be obtained. The method according to the invention allows especially deposition of AGM granules on fast moving carrier layers at surface speeds of 1 m/sec up to 3 m/sec, preferably up to 5 m/sec, or even 10 m/sec and even more preferably up to 15 m/sec with high accuracy. Because of the accuracy of the deposition of AGM granules, the invention allows manufacturing of e.g. an absorbent core without cellulose or similarly absorbent and/or hydrophilic fibers in diapers which results in extreme core thinness and improved comfort and fit in use for the articles.

The term "transfer device" as used herein includes any moveable member being capable of taking up AGM granules in a predetermined shape and a thickness profile and depositing the granules-without amending the configuration thereof-on a carrier substrate.

A preferred embodiment of the transfer device is a patterned rotary drum or roll, which is called "printing roll" or "transfer roll" in the present context because the transfer of a pattern of AGM granules can be comparable with printing. Another embodiment would be a moveable belt having recesses on the surface and being moved between the AGM granule bulk storage and the transfer position.

The term "bulk" or "bulk storage" of AGM granules refer in the present context to any kind of supply of granules, particularly a hopper.

"Retaining means" are provided to keep the AGM granules taken up by the recesses of the transfer device in these recesses during movement from the bulk to the transfer position where the granules are delivered to the carrier layer. In one preferred embodiment the retaining means is a belt, which is guided along the surface of the transfer device, particularly the printing roll, on the way from the bulk to the transfer position. Other possible embodiments, which are particularly preferred are vacuum means for keeping the AGM granules in the recesses. Also the use of an electrostatic field is possible "Expelling means" in the present context means delivering the AGM granules in the transfer position as defined above to a carrier substrate. For delivering the granules, the granules may be expelled by air jets or an electrostatic field or just by gravity.

BRIEF DESCRIPTION OF THE DRAWINGS

The above and further features, aspects and advantages of the present invention will become better understood with regard to the following description making reference to the accompanying drawings.

DETAILED DESCRIPTION OF THE INVENTION

Figure 1:
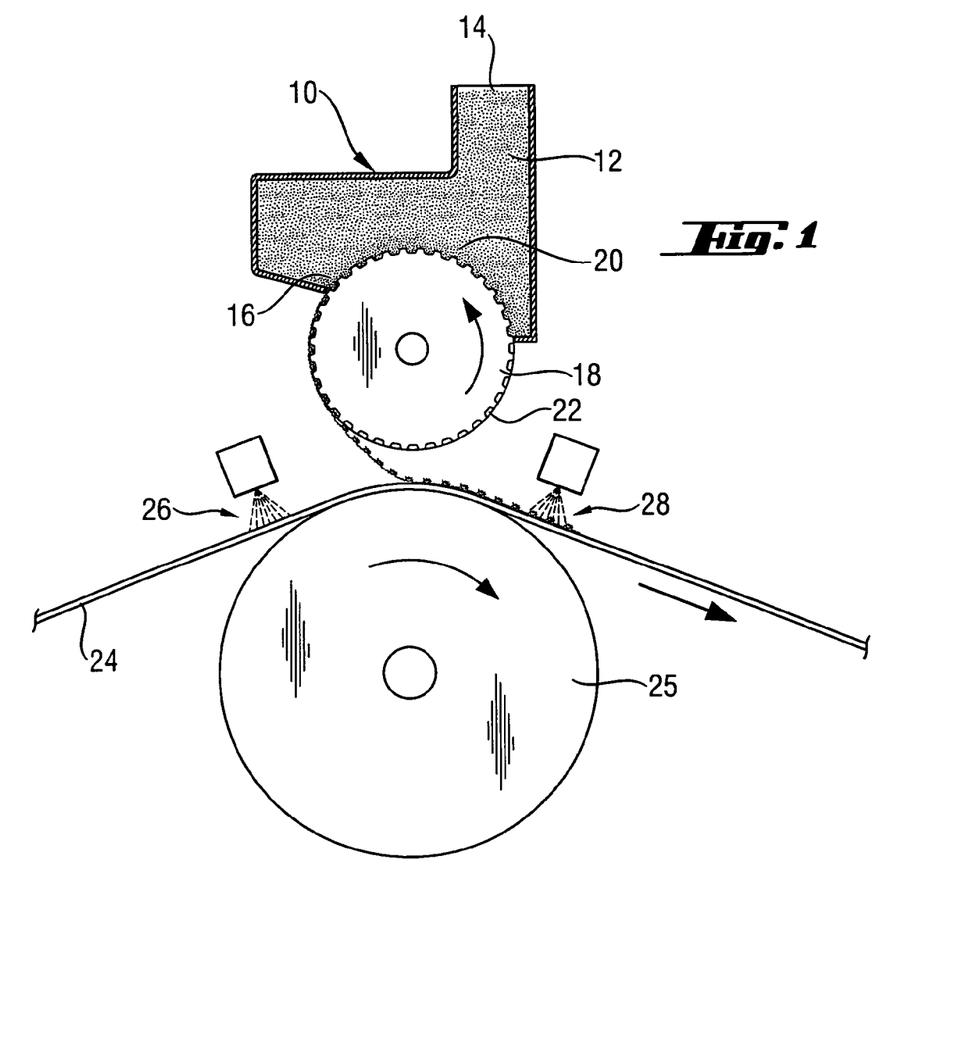
FIG. 1 illustrates one embodiment of the present invention.

FIG. 1 shows a hopper (10) filled with a bulk of AGM material (12). The hopper (10) has a supply opening (14) on the upper side and a delivery opening (16) at the bottom. The hopper forms one embodiment of what is called "bulk" in the present context.

A printing roll (18) enters into the opening (16) in the hopper (10) in a way that the bottom of the hopper surrounding the opening (16) closely follows the contour of the roller (18) and an unintended drop out of AGM granules is prevented.

The printing roll (18) is provided with holes or recesses (22) on the surface thereof which are filled with AGM granules from the lower end (20) of the bulk of AGM material (12) in the hopper (10), while the surface of the roll (18) passes through the AGM material (12) inside the hopper (10). The number, the size and the position of the recesses (22) are selected such that the volume and the pattern of the recesses correspond to the intended pattern and thickness profile of the AGM material which is to be received by the printing roll and to be transferred to a carrier layer as will be explained below.

The printing roll (18) forms one embodiment of a transfer device according to the present invention. Another embodiment could for instance be formed by a belt having recesses in the surface thereof for receiving AGM material.

A rotatable printing roll however may be a preferred embodiment.

The AGM granules are taken up by the recesses (22) of the printing roll (18) when one of the recesses (22) on the transfer roll (18) is in this loading position. The AGM granules are retained in these recesses on the way from the hopper (10) to a position called "transfer or meeting position" herein where the printing roll (18) which is rotated in counter clockwise direction in FIG. 1 is in a position immediately opposite the surface of a carrier layer (24). The carrier layer (24) is supported by a rotating support roll (25).

The carrier layer is for instance a non-woven web onto which the AGM granules are expelled or laid down (by gravity) from the printing roll. For holding the AGM granules on the carrier layer (24), glue is preferably sprayed onto the carrier layer (24) upstream the transfer position between the printing roll (18) and the carrier layer (24), which upstream position is designated by reference numeral (26). Because the glue is applied in this upstream position (26) onto the carrier layer (24), the AGM granules are retained on the carrier layer (24). A particularly preferred glue for retaining the AGM granules on the carrier layer (24) is a micro fiber glue with very thin fiber made by spraying a hot melt adhesive material through respectively thin nozzles. Such nozzles are commercially available from Nordson Company, Dawsonville, Ga., USA.

It is preferred that the support roll (25), which could alternatively also be provided by a moving belt, is also holding the AGM particles down onto the carrier, especially by use of a pressure differential (vacuum) through a screen forming the cylindrical surface of the support roll (25). In another position downstream the transfer position between the printing roll (18) and the carrier layer (24), which position is designated by (28), glue is—preferably but optional—sprayed onto the AGM granules on the carrier layer (24), which glue preferably is also a microfilament glue entering like fibers between the granules of the AGM to hold the whole deposit together. In an alternative embodiment it is also possible to apply a cover layer carrying glue onto the AGM granules.

When large amounts of glue are applied at positions (26) and/or (28) it is advantageous to use materials for the cylindrical support roll surface, which have a low or no tendency to accumulate adhesive residue. This can be Teflon™ coated surfaces or if a belt instead of a support roll is used, silicon rubber materials. Especially in case the carrier layer (24) is exposed to a vacuum on the inside of the support roll the surface of the support roll can be made of a silicon rubber screen (preferably metal reinforced).

As shown in FIG. 1, in this particular embodiment the printing roll (18) is moving through the AGM material by rotation of the roll in the counterclockwise direction designated by the arrow in FIG. 1, AGM granules are taken up in the recesses (22) of the roll, but there is of course a certain risk that additional AGM granules beyond those filling the recesses are carried out of the hopper between the surface of the printing roll (18) and adjacent edge of the bottom of the hopper. Therefore, scraping means (19) are provided at this edge one example of which is shown in FIG. 2.

Figure 2:
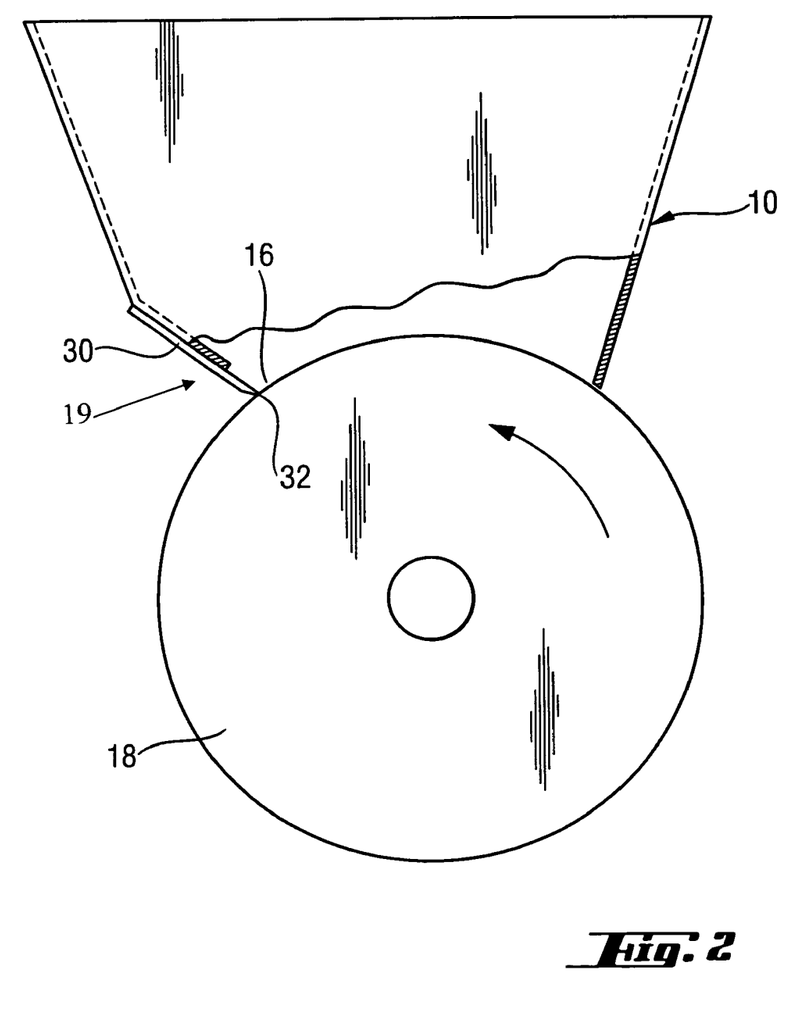
FIG. 2 is a diagrammatic illustration of the embodiment of FIG. 1 showing an additional detail.

In FIG. 2 those members or elements which have been already described in connection with FIG. 1, are designated by the same reference numerals.

The scraping means (19) in FIG. 2 are formed by a doctor blade (30) having a scraping edge (32) being in close contact with the surface of the printing roll (18). The distance between the doctor blade (30) and the printing roll (18) should be above 0 mm to prevent excess pressures and damage to the equipment and the AGM particles. The particle size mix is one of the factors to consider when selecting the scraping blade distance. E.g. very large AGM particles with mean diameter of 900 micrometer and above would need a spacing of less than 900 micrometer. The upper useful spacing limit should be about 1 mm with the preferred spacing between 0.01 and 0.5 mm, more preferably between 0.03 and 0.1 mm to ensure good scraping at extended production runs.

Figure 3:
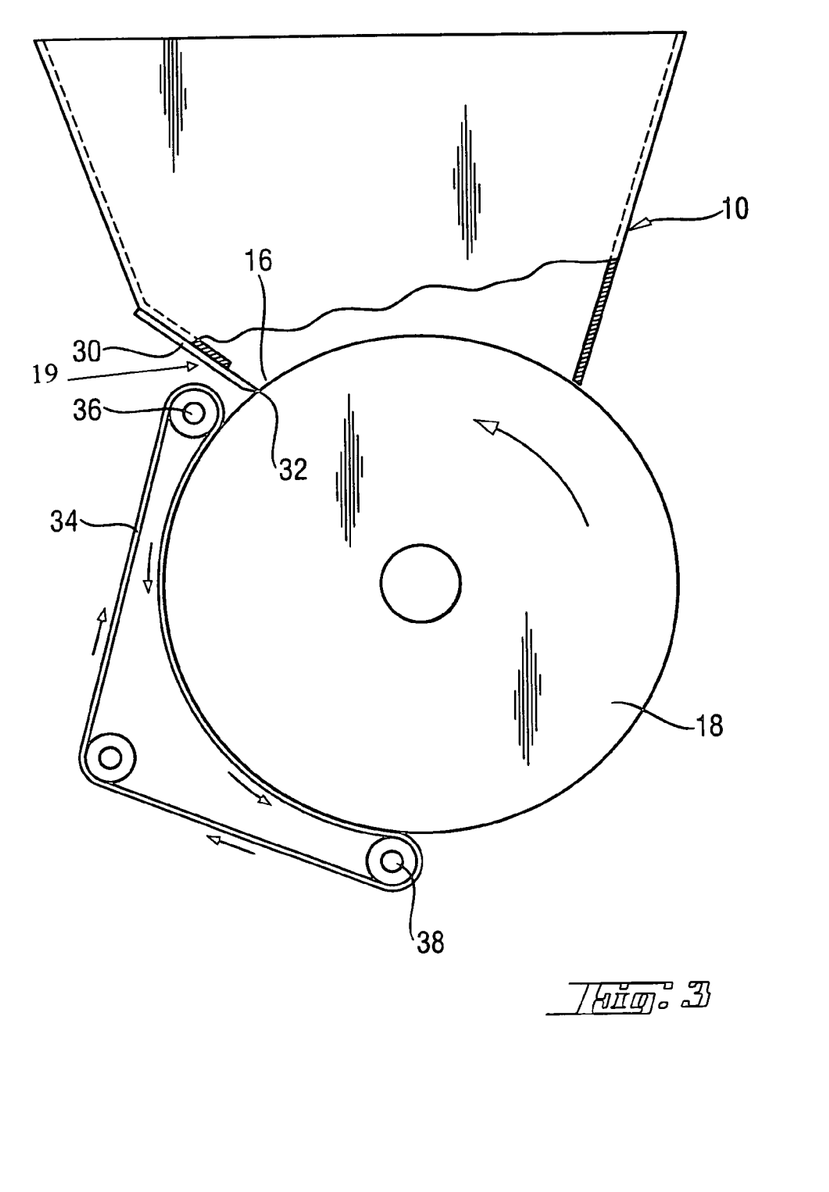
FIG. 3 illustrates a modification of the embodiment of FIG. 2.

FIG. 3 illustrates an embodiment corresponding to the embodiment of FIG. 2 but additionally showing retaining means for retaining the AGM granules in the recesses (not shown) provided in the surface of the printing roll (18) on the way from the hopper (10) to the transfer position.

One possibility to hold the AGM granules in the recesses may be a vacuum applied to the inner side of the printing roll (18) in combination with suction holes (not shown) in the bottom of the recesses. Another embodiment of retaining means as shown in FIG. 3 is formed by an endless belt (34) which is moved together with the rotation of the printing roll (18) along with the surface thereof from a position immediately downstream the doctor blade to a position immediately upstream the transfer position where the granules are transferred to the carrier layer (24) not shown in FIG. 3. The belt is driven around an upper and a lower guide roll (36,38) in the upper and lower position of the path of the belt adjacent the printing roll (18) and around a third guide roll spaced from the surface of the printing roll and forming a triangle with the other guide roll (36,38). The belt (34) may be driven by driving one of these three rolls to move the belt (34) in the direction marked by arrows. Alternatively, the belt may be idling and moved by contact with the surface of the printing roll (18).

Figure 4:
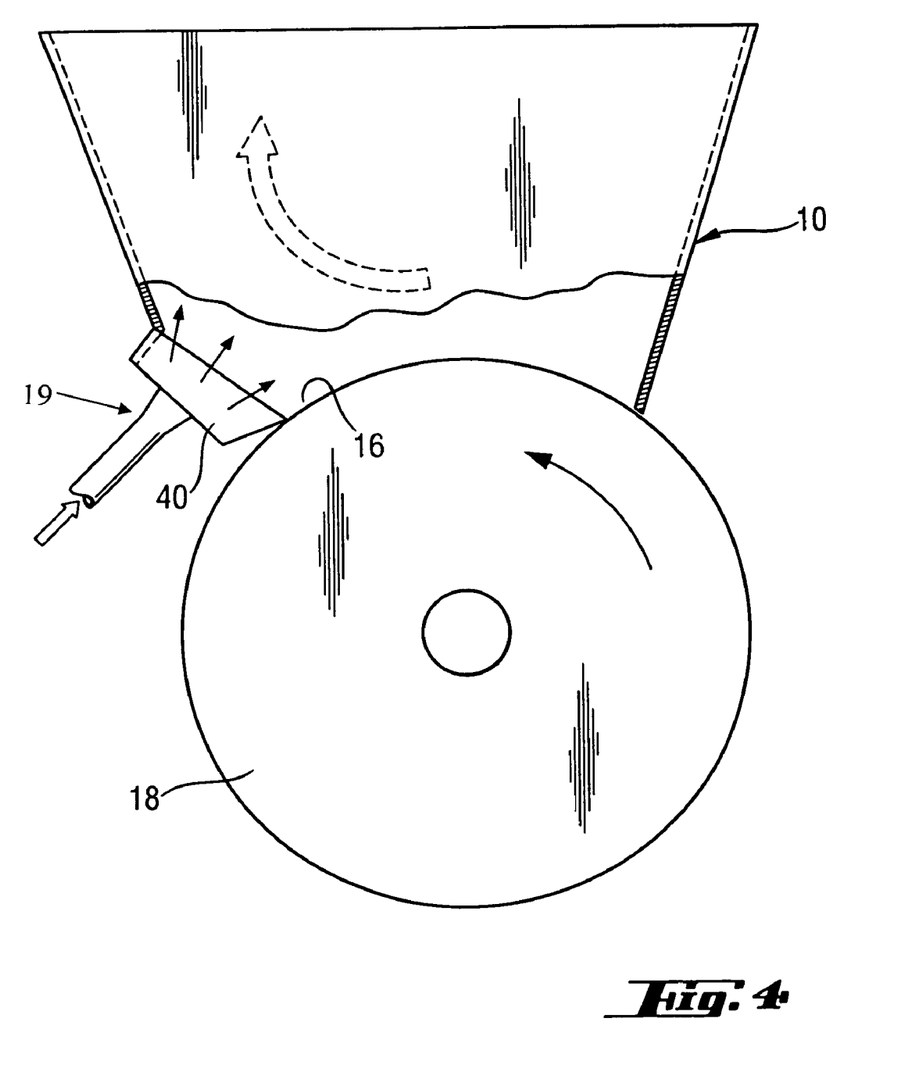
FIG. 4 corresponds to FIG. 2 with a modification of one feature.

FIG. 4 shows an alternative embodiment of the scraping means (19) of FIGS. 2 and 3. The reference numerals of FIGS. 2 and 3 are also used in FIG. 4 for corresponding parts. Instead of the doctor blade of FIGS. 2 and 3, the embodiment of FIG. 4 is provided with an air jet box (40) arranged in the position of the doctor blade (30) of FIGS. 2 and 3 and ejecting air under pressure opposite to the moving direction of the surface of the printing roll (18), as shown in FIG. 4, to keep the AGM granules back from the gap between the air jet box and the surface of the printing roll 18.

Figure 5:
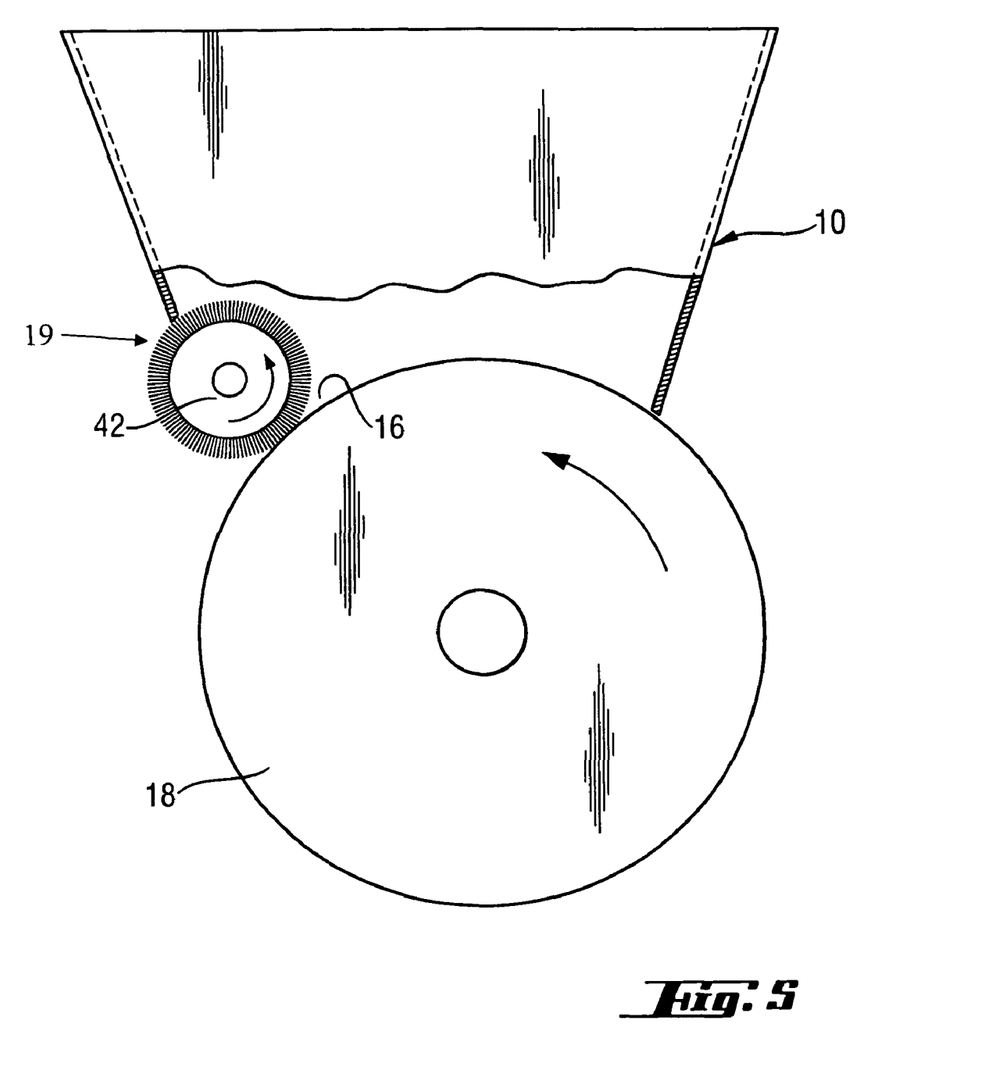
FIG. 5 again corresponds to FIG. 2 with a modification of one feature.

The embodiment of FIG. 5 which again basically corresponds to the foregoing embodiments of FIG. 2 to 4 shows another modification of the scraping means (19) which in this case are formed by a rotatable brush (42) in the position of the doctor blade mentioned before to keep the AGM granules back from leaving the hopper 10 by rotation in counter clockwise direction.

FIG. 6 again shows another embodiment of the scraping means (19), which in this case is formed by a moveable belt running around a lower and an upper guide roll (46,48) one of which may be driven by a suitable drive not shown. The belt (44) moves on the side of the AGM materials substantially vertically upward as shown by the arrow and returns down on the outer side of the hopper (10).

Figure 6:
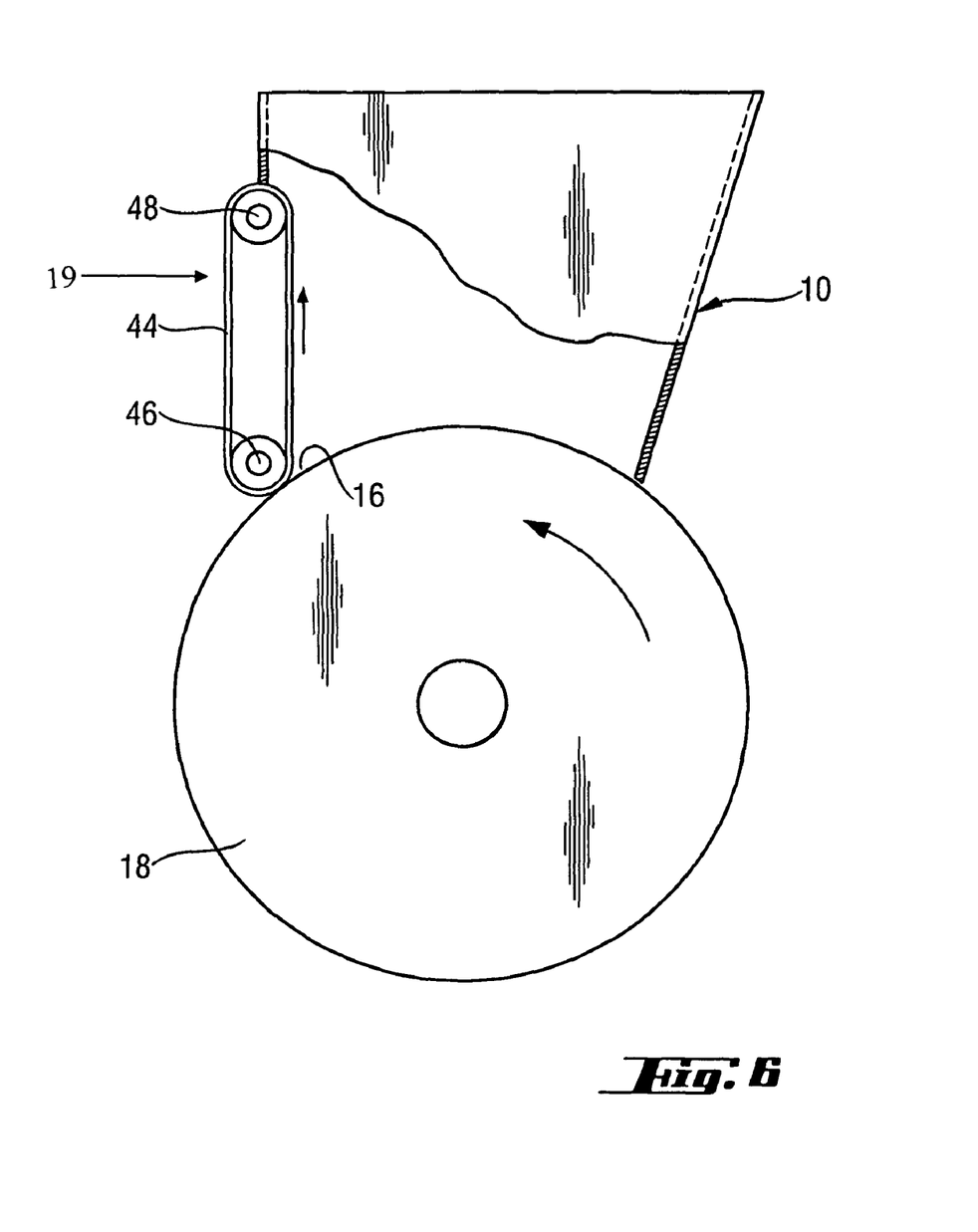
FIG. 6 again corresponds to FIG. 2 with a modification of one feature.

The belt (44) lifts the AGM material on the inner side of the hopper (10) to keep the AGM material away from leaving the hopper through the gap between the surface of the printing roll and the belt (44).

Figure 7:
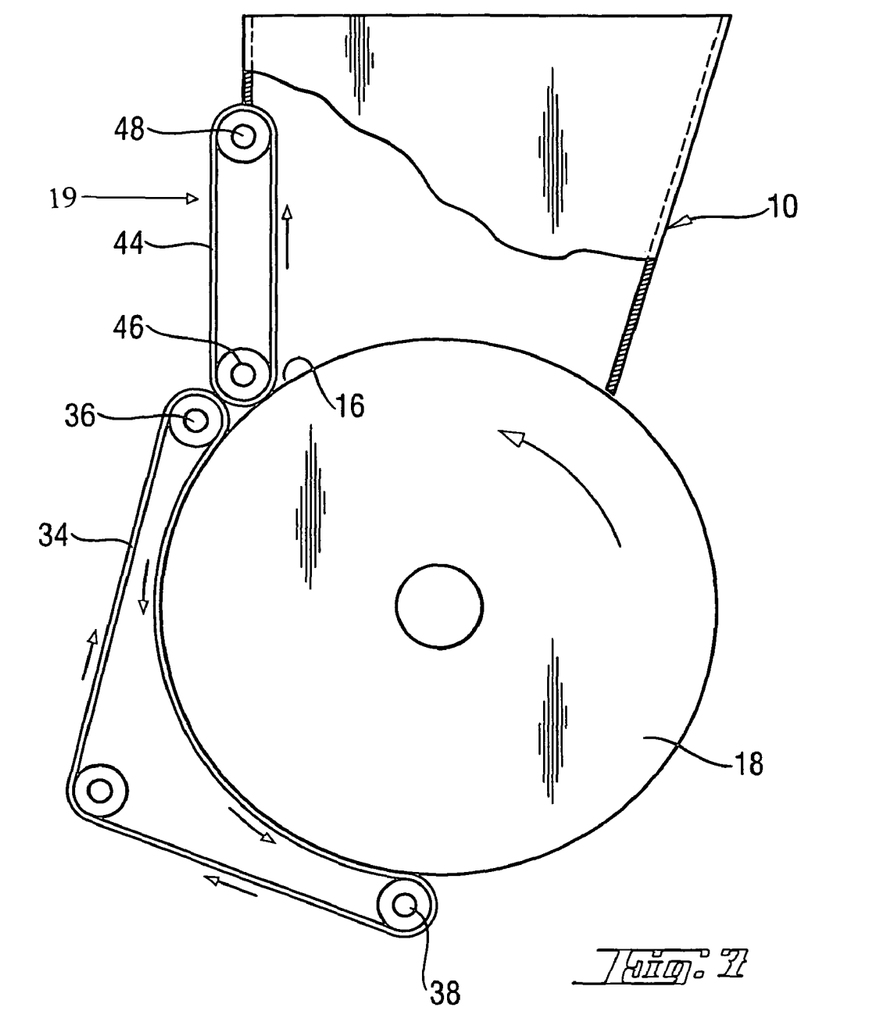
FIG. 7 shows an embodiment being a combination of FIG. 3 and 6.

FIG. 7 shows an embodiment which is substantially a combination of the embodiments of FIGS. 3 and 6, comprising a belt (34) for retaining the AGM granules in the recesses of the printing roll and another belt (44) with the function of scraping means as discussed in connection with FIG. 6.

Figure 8:
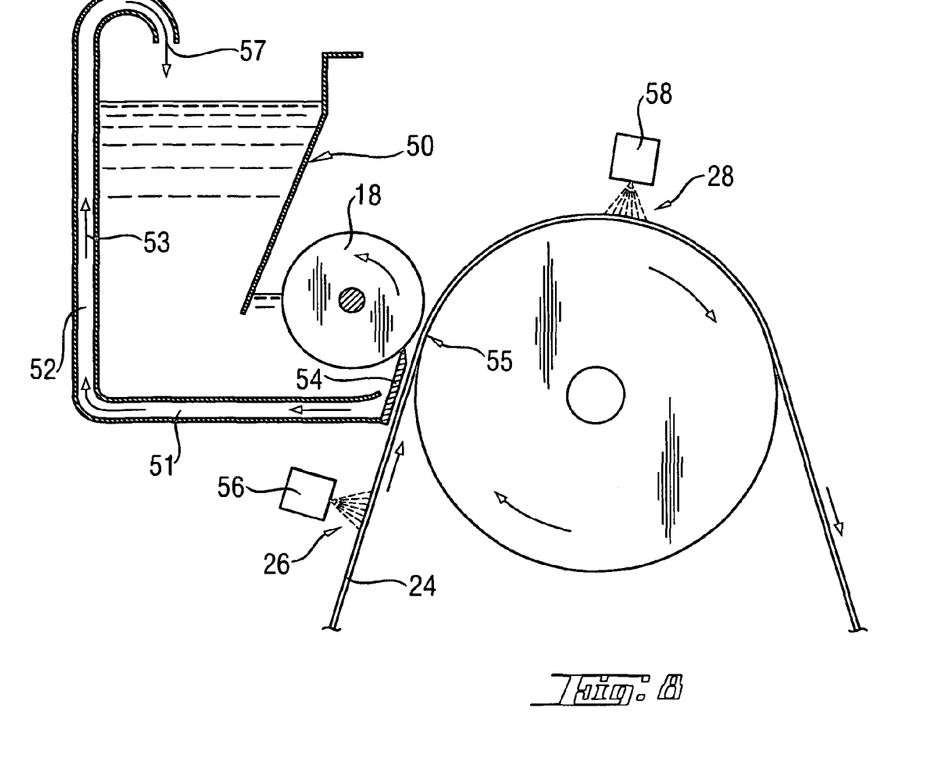
FIG. 8 shows another embodiment of an apparatus according to the invention and for conducting the methods according to the invention.

FIG. 8 shows an embodiment the hopper (50) of which is formed as a fluidized bed for keeping the AGM granules in a floating state. The printing roll designated by (18) in this case rotates through the fluidized granules which are taken up by the recesses in the surface of the printing roll (18).

AGM granules extending beyond the recesses or adhering to the surface of the printing roll (18) outside the recesses are stripped away from the printing roll by a doctor blade (54) acting as scraping means and being arranged in a position immediately upstream the meeting position designated by (55) in this case where the printing roll is positioned immediately opposite the carrier layer (24) supported by the lay down drum. In the positions (26,28) upstream and downstream the meeting position there are position glue heads (56,58) for applying glue onto the carrier layer (24) in the position (26) and onto the deposited AGM granules in the position (28) applied onto the carrier layer. In this case, the printing roll immerges into the AGM bulk storage from the top.

In preferred embodiment, the system shown in FIG. 8 further comprises an airborne particle cycling system (51, 52, 57). In this system particles are transported from a location close to the meeting position (55) along conducts (51, 52) in the direction of arrow (53) to a return conduct end (57). In this way the particles are prevented from being stuck or settling in the region of meeting position (55) due to agitation reduction in that region of the fluidized bed. The particle cycling system usually can be operated by an air current in the pipe transporting the particles along the conducts.

Figure 9:
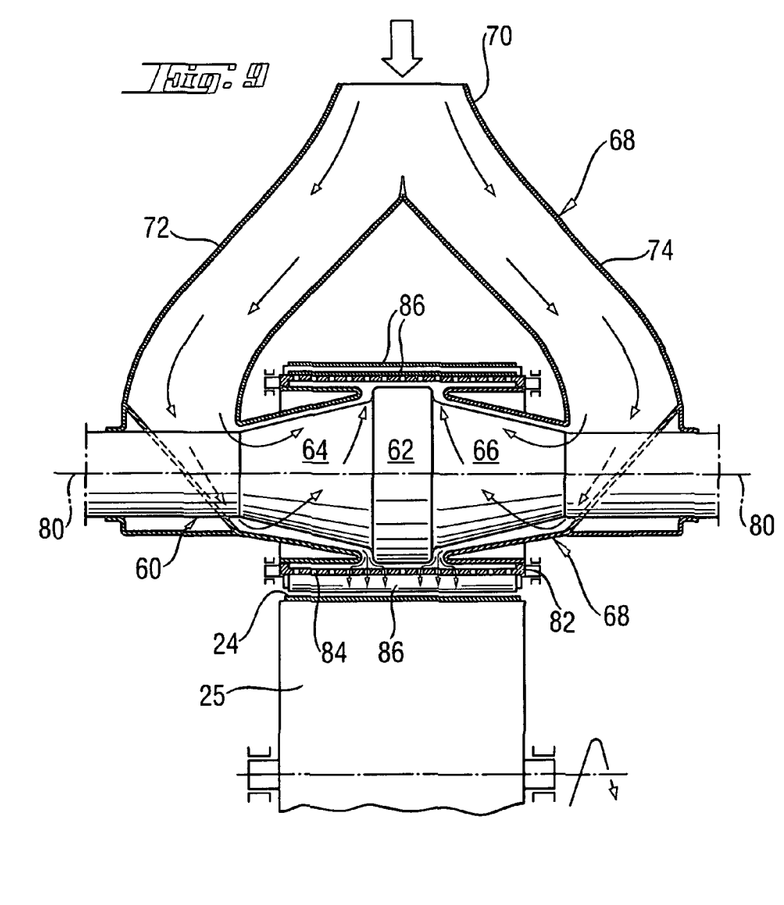
FIG. 9 is a cross section along line 9-9 of another embodiment of the invention shown in FIG. 10.
Figure 10:
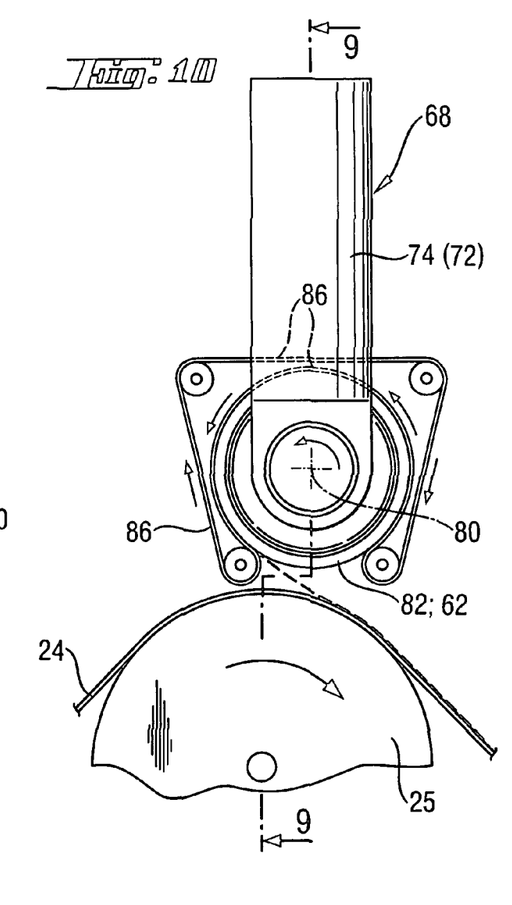
FIG. 10 is a front view from the left side in FIG. 9.

In FIG. 9, there is shown an indirect particle printing station comprising an AGM supply (70, 72, 74) connected to a stator housing (68), centrifugal roll (60) having its axis (80) along a horizontal line from left to right in FIG. 9. FIG. 9 is a cross section view along line 9 in FIG. 10, which is showing a side view of the particle printing station of FIG. 9. In FIG. 10 the carrier onto which AGM is deposited is shown on a transport cylinder also referred to a support roll (25, partially shown). The centrifugal roll (60) comprises a central portion (62) of cylindrical form and two frustoconical inlet portions (64, 66) on both sides thereof in axial direction. The inlet portions (64, 66) are connected with an AGM supply system (68) formed by a supply tube (70) divided in two branch tubes (72, 74) which are connected with the inlet portions (64, 66) of the centrifugal roll (60) at their axial ends. Thus AGM is supplied through the supply tube (70) into the branch tubes (72, 74) and transported in the inlet portions (64, 66) by centrifugal forces and finally into the central portion (62) of the centrifugal roll. At this position the AGM leaves the centrifugal roll and the stator (68) and, still by centrifugally created pressure is pressed against the inside of the screen printing roll (82) which is partially covered on the outside with a belt(86).

This printing roll is provided with openings (not shown) in the circumferential wall forming a pattern of suitable shape and size through which, at each rotation of the centrifugal roll, AGM granules leave the printing station and are deposited without contact on a carrier layer (24) (as shown in FIG. 10).

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with a definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for indirectly applying absorbent gelling material granules onto a carrier layer for use in an absorbent article, particularly a diaper, which article comprises said carrier layer together with further layers, said method comprises the following steps:

absorbent gelling material granules are taken up by a transfer device from a bulk storage of absorbent gelling material granules, said transfer device having a surface with recesses, said recesses having an absorbent gelling material surface and an opposed inside, wherein the number, size and position of said recesses determine the amount and pattern of absorbent gelling material granules taken up by said transfer device, said transfer device being moveable from a loading position adjacent to the bulk storage to a meeting position at which the carrier layer is adjacent to the transfer device means being provided for retaining said absorbent gelling material granules inside said recesses during movement of said transfer device to said meeting position, and means being provided for expelling said absorbent gelling material granules onto said carrier layer at said meeting position;

wherein a first glue is applied onto said carrier layer upstream of said meeting position before absorbent gelling material granules are deposited onto said carrier layer from said transfer device in said meeting position and wherein a second glue is applied onto said absorbent gelling material granules after said absorbent gelling materal granules have been deposited onto said carrier layer;

wherein at least one of said first and second glues is a micro-fiber glue.

2. Method as claimed in claim 1 wherein a cover layer carrying glue is applied onto said absorbent gelling material granules downstream said meeting position.

3. Method as claimed in claim 1 wherein said transfer device is a transfer roll, said transfer roll is provided with said recesses on the surface thereof.

4. Method as claimed in claim 1 wherein said carrier layer is transported to and from said meeting position by means of a conveying belt or a rotating support roll.

5. Method as claimed in claim 1 wherein said means for retaining said absorbent gelling material granules in said recesses of said transfer device comprises a vacuum applied to the recesses from said inside of said transfer device.

6. Method as claimed in claim 1 wherein said expelling means for expelling the absorbent gelling material granules from said transfer device onto said carrier layer comprises air jet means.

7. Method as claimed in claim 1 wherein said absorbent gelling material is contained in a hopper having an open bottom passed by said transfer device, whereby said absorbent gelling material granules are filling said recesses of said transfer device by gravity.

8. Method as claimed in claim 1 wherein said absorbent gelling material bulk storage is a container comprising a bed of absorbent gelling material granules and having an open top passed by said transfer device such that said transfer device extends into said bed of absorbent gelling material granules in order for said absorbent gelling material granules to be lifted up into said recesses in said transfer device by applying a vacuum from said inside of said recesses.

9. Method as claimed in claim 1 further using scraping means for holding back absorbent gelling material granules from being moved by said transfer device in excess of the amount required to fill the volume of said recesses.

10. Method as claimed in claim 9 wherein said scraping means is formed by a doctor blade, the distance of which to said transfer means is above 0 mm and up to 1 mm.

11. An apparatus for carrying out the process of claim 1, said apparatus comprising a transfer device for taking up absorbent gelling material granules from a bulk storage of absorbent gelling material granules, said transfer device having recesses on its surface, the number, the size and position of said recesses determining the amount and pattern of absorbent gelling material granules taken up by said transfer device, said transfer device being moveable from said bulk storage to a position where the carrier layer is passing the transfer device.

12. The apparatus as claimed in claim 11, wherein said transfer device is a rotating roll.

* * * * *